United States Patent
Field

(10) Patent No.: US 9,057,677 B2
(45) Date of Patent: Jun. 16, 2015

(54) METHODS AND SYSTEMS FOR MONITORING LIQUIDS

(71) Applicant: EMPIRE TECHNOLOGY DEVELOPMENT LLC, Wilmington, DE (US)

(72) Inventor: Christopher David Field, Manly Vale (AU)

(73) Assignee: Empire Technology Development LLC, Wilmington, DE (US)

( * ) Notice: Subject to any disclaimer, the term of this patent is extended or adjusted under 35 U.S.C. 154(b) by 26 days.

(21) Appl. No.: 13/825,052

(22) PCT Filed: Nov. 6, 2012

(86) PCT No.: PCT/US2012/063659
§ 371 (c)(1),
(2) Date: Mar. 19, 2013

(87) PCT Pub. No.: WO2014/074087
PCT Pub. Date: May 15, 2014

(65) Prior Publication Data
US 2014/0127742 A1 May 8, 2014

(51) Int. Cl.
*H04B 11/00* (2006.01)
*G01S 1/72* (2006.01)
*G01N 29/032* (2006.01)
*G01N 29/34* (2006.01)
*G01N 29/46* (2006.01)

(52) U.S. Cl.
CPC .............. *G01N 29/032* (2013.01); *G01S 1/72* (2013.01); *H04B 11/00* (2013.01); *G01N 29/343* (2013.01); *G01N 29/346* (2013.01); *G01N 29/348* (2013.01); *G01N 29/46* (2013.01); *G01N 2291/02809* (2013.01); *G01N 2291/02881* (2013.01); *G01N 2291/048* (2013.01)

(58) Field of Classification Search
CPC .................................. H04B 11/00; G01S 1/72
USPC ........................................... 367/117, 137, 140
See application file for complete search history.

(56) References Cited

U.S. PATENT DOCUMENTS

| 5,854,589 A | 12/1998 | How et al. |
| 5,947,256 A | 9/1999 | Patterson |
| 6,093,338 A | 7/2000 | Tani et al. |

(Continued)

FOREIGN PATENT DOCUMENTS

WO    WO 03/087955 A1    10/2003

OTHER PUBLICATIONS

International Search Report and Written Opinion for PCT/US2012/063659 dated Jan. 31, 2013.

(Continued)

*Primary Examiner* — Paul Hyun
(74) *Attorney, Agent, or Firm* — Pepper Hamilton LLP

(57) ABSTRACT

Technologies are generally disclosed for systems and methods for monitoring a liquid. An illustrative method may include disposing one or more sensors in the liquid, sensing one or more properties exhibited by the liquid using the one or more sensors, producing sensed data from the properties by the one or more sensors, encoding the sensed data into an acoustic signal by the one or more sensors, transmitting the acoustic signal through the liquid by the one or more sensors and receiving the acoustic signal by one or more sound receiving devices.

22 Claims, 7 Drawing Sheets

(56) References Cited

U.S. PATENT DOCUMENTS

| | | | |
|---|---|---|---|
| 2003/0205187 A1 | 11/2003 | Carlson et al. | |
| 2004/0064979 A1 | 4/2004 | Smith et al. | |
| 2004/0066313 A1* | 4/2004 | Ong et al. | 340/870.11 |
| 2005/0080520 A1 | 4/2005 | Kline et al. | |
| 2005/0192727 A1 | 9/2005 | Shostak et al. | |
| 2006/0283252 A1 | 12/2006 | Liu et al. | |
| 2007/0204691 A1* | 9/2007 | Bogner et al. | 73/432.1 |
| 2008/0279047 A1* | 11/2008 | An et al. | 367/134 |
| 2009/0141591 A1* | 6/2009 | Basilico | 367/128 |
| 2011/0172931 A1 | 7/2011 | Murthy | |

OTHER PUBLICATIONS

Acoustic Tag, http://en.wikipedia.org/wiki/Acoustic_tag (Printed from Internet Jan. 9, 2013).

Acoustic Telemetry, http://www.htisonar.com/micro)htm (Printed from Internet Jan. 9, 2013).

Crocker, Handbook of Acoustics, John Wiley & Sons Inc. (Mar. 1998).

Foodborne Illness, http://en.wikipedia.org/wiki/Foodborne_illness (Printed from Internet Feb. 25, 2013).

Grout et al., Contaminated liquid nitrogen vapour as a risk factor in pathogen transfer, *Theriogenology* (Apr. 15, 2009), 71(7):1079-1082 (Abstract).

Kitsunai et al., Development of Miniature Needle-Type Hydrophone with Lead Zirconate Titanate Polycrystalline Film Deposited by Hydrothermal Method, *Japanese Journal of Applied Physics* (2006), 45(5B):4688-4692.

Pros and Cons of RFID, http://www.ferret.com.au/c/GSI-Austalia/PROS-AND-CONS-Of-RFID-n719191 (Printed from Internet Feb. 25, 2013).

Sonar, http://en.wikipedia.org/wiki/Sonar (Printed from Internet Jan. 9, 2013).

CSIRO Marine and Atmospheric Research:, Accessed at http://web.archive.org/web/20120326014341/http://www.cmar.csiro.au/tagging/tags/acoustic.htm, accessed on Aug. 21, 2014, pp. 2.

De Moura et al., "Independent Component Analysis for Passive Sonar Signal Processing," Advances in Sonar Technology, Chapter 5, pp. 92-110 (Feb. 2009).

Environmental dumping, accessed at http://en.wikipedia.org/wiki/Environmental_dumping, accessed on Aug. 21, 2014, pp. 5.

Helping Meteorologists and Oceanographers Worldwide, accessed at http://web.archive.org/web/20121015131333/http://www.jcommops.org/dbcp, accessed on Aug. 21, 2014, pp. 2.

International Search Report and Written Opinion for PCT/US2012/038783 dated Dec. 7, 2012.

Mathias, Reducing the global impact of e-waste, accessed at http://ewasteguide.info/node/3761, Jan. 24, 2008, pp. 1.

Tindal, Satellite meets sonar, links submarines to real world, accessed at http://www.zdnet.com/satellite-meets-sonar-links-submarines-to-real-world-1339283951/, accessed on Aug. 21, 2014, pp. 3.

Ultrasonic 3D Tagging System: Technology for Observing Human Activity in the Order of Centimeters, accessed at http://web.archive.org/web/20130213030813/http://www.dh.aist.go.jp/en/research/function/Ultrasonic3DTag/, accessed on Aug. 21, 2014, pp. 5.

What do the Codes Mean?, accessed at http://web.archive.org/web/20080827225700/http://www.morethanyouthink.com/shopping/countrycodes.html, accessed on Aug. 21, 2014, pp. 2.

Why do we know so much about the supply chain and so little about the 'removal-chain'?, accessed at http://web.archive.org/web/20121101044617/http://senseable.mit.edu/trashtrack/, accessed on Aug. 21, 2014, pp. 2.

World Meteorological Organization, accessed at http://web.archive.org/web/20121103000018/http://www.wmo.int/pages/index_en.html, accessed on Aug. 21, 2014, pp. 1.

Zhou et al., Piezoelectric films for high frequency ultrasonic transducers in biomedical applications, *Progress in Materials Science*, vol. 56, No. 2, pp. 139-174 (2011).

* cited by examiner

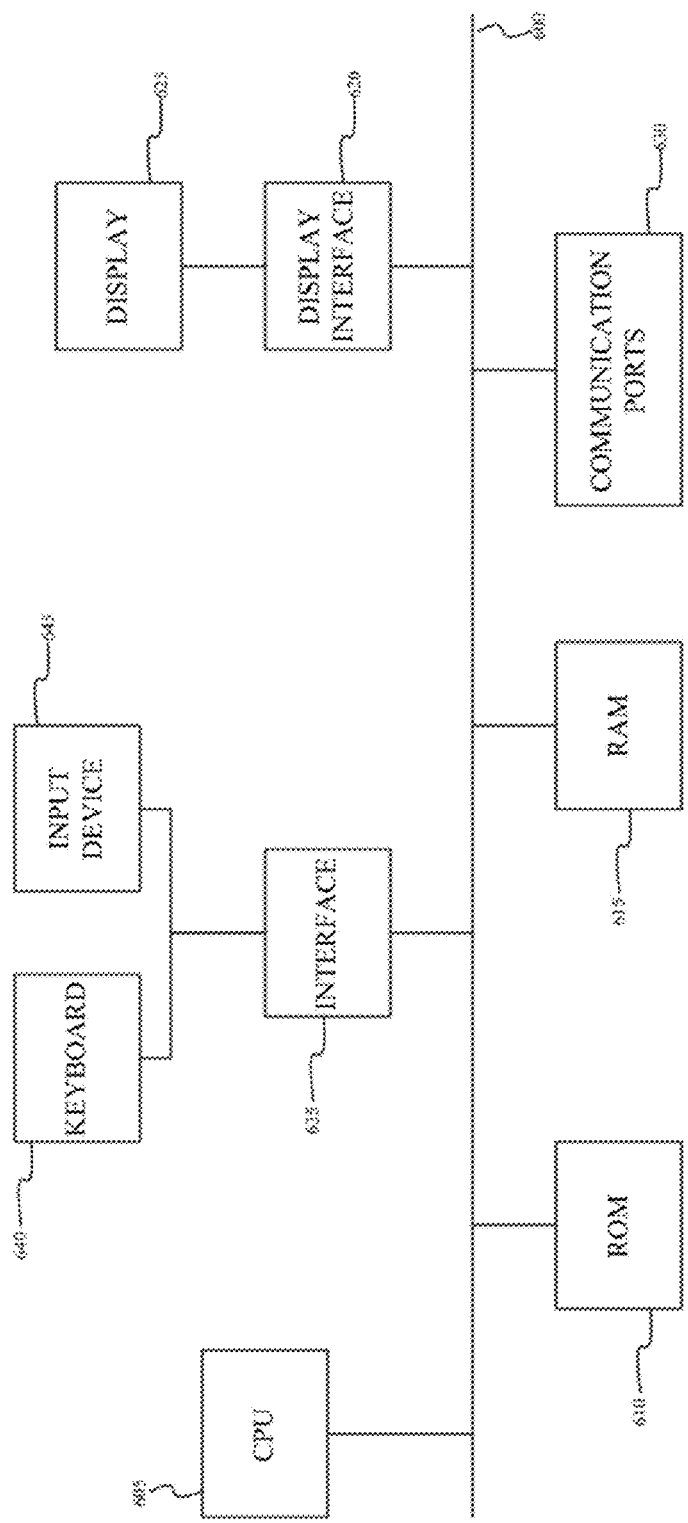

METHODS AND SYSTEMS FOR MONITORING LIQUIDS

CLAIM OF PRIORITY

This application is a U.S. national stage filing under 35 U.S.C. §371 of International Application No. PCT/US2012/063659, filed Nov. 6, 2012 and entitled "Methods and Systems for Monitoring Liquids," the disclosure of which is incorporated by reference in its entirety.

BACKGROUND

The packaging of liquid products, particularly perishable liquids such as food, beverages, alcohol, fuels, chemicals, medical fluids and the like, must be completed with materials and systems that attempt to prevent damage, spoilage and the like before the product is used. As a result, sustainable product packaging has been developed, such as packaging that extends the shelf-life of a product, packaging that reduces product damage, packaging that decreases the product's environmental footprint during its life-cycle and/or product packaging that is capable of communicating information regarding the safety of the product housed within. Prior solutions have included printing a "best by" date on the product packaging to notify a consumer of the expected date of product spoilage. However, use of the "best by" date is rudimentary at best, as it requires a great deal of guess work, and because product producers commonly err on the side of caution and provide "best by" dates that are well in advance of the actual expected date of spoilage, thus resulting in wasted products.

Thus to solve this issue, there has been increased interest in the use of packaging that is capable of communicating information regarding the safety of the product housed within, which is sometimes referred to as "intelligent packaging." Intelligent packaging may be interactive and may include information gathered or measured from the contained product.

Currently, no systems and methods exist for affordably providing an intelligent packaging that incorporates a plurality of sensors to monitor the product within, and can additionally transmit the data in real time. Thus, there exists a need for product packaging that is cost effective for widespread use, sustainable, incorporates sensors for monitoring the product and can transmit monitoring data.

SUMMARY

In an embodiment, a system for monitoring a liquid may include one or more sensors configured to sense one or more properties of the liquid and transmit an acoustic signal encoded with sensed data regarding the properties through the liquid and one or more sound receiving devices configured to receive the acoustic signal transmitted by at least one sensor.

In an embodiment, a method of monitoring a liquid may include disposing one or more sensors in the liquid, sensing one or more properties exhibited by the liquid using the sensors, producing sensed data from the properties by the sensors, encoding the sensed data into an acoustic signal by the sensors, transmitting the acoustic signal through the liquid by the sensors and receiving the acoustic signal by one or more sound receiving devices.

In an embodiment, an article of manufacture may include a container for holding a liquid, one or more sensors disposed within the container, configured to sense one or more properties of the liquid and transmit an acoustic signal encoded with sensed data regarding the properties through the liquid, and one or more sound receiving devices configured to receive the acoustic signal transmitted by at least one sensor.

BRIEF DESCRIPTION OF THE DRAWINGS

FIG. 6 depicts a block diagram of illustrative internal hardware that may be used to contain or implement program instructions according to an embodiment.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The following terms shall have, for the purposes of this application, the respective meanings set forth below.

An "electronic device" generally refers to any type of device that is capable of communicating with the various elements disclosed herein. The electronic device further refers to a device that includes a processor and a tangible, computer-readable memory. The memory may contain programming instructions that, when executed by the processor, cause the device to perform one or more operations according to the programming instructions. Examples of electronic devices include personal computers, gaming systems, televisions and portable electronic devices such as smartphones, personal digital assistants, cameras, tablet computers, laptop computers, GPS navigation devices, media players and the like.

Figure 1A:
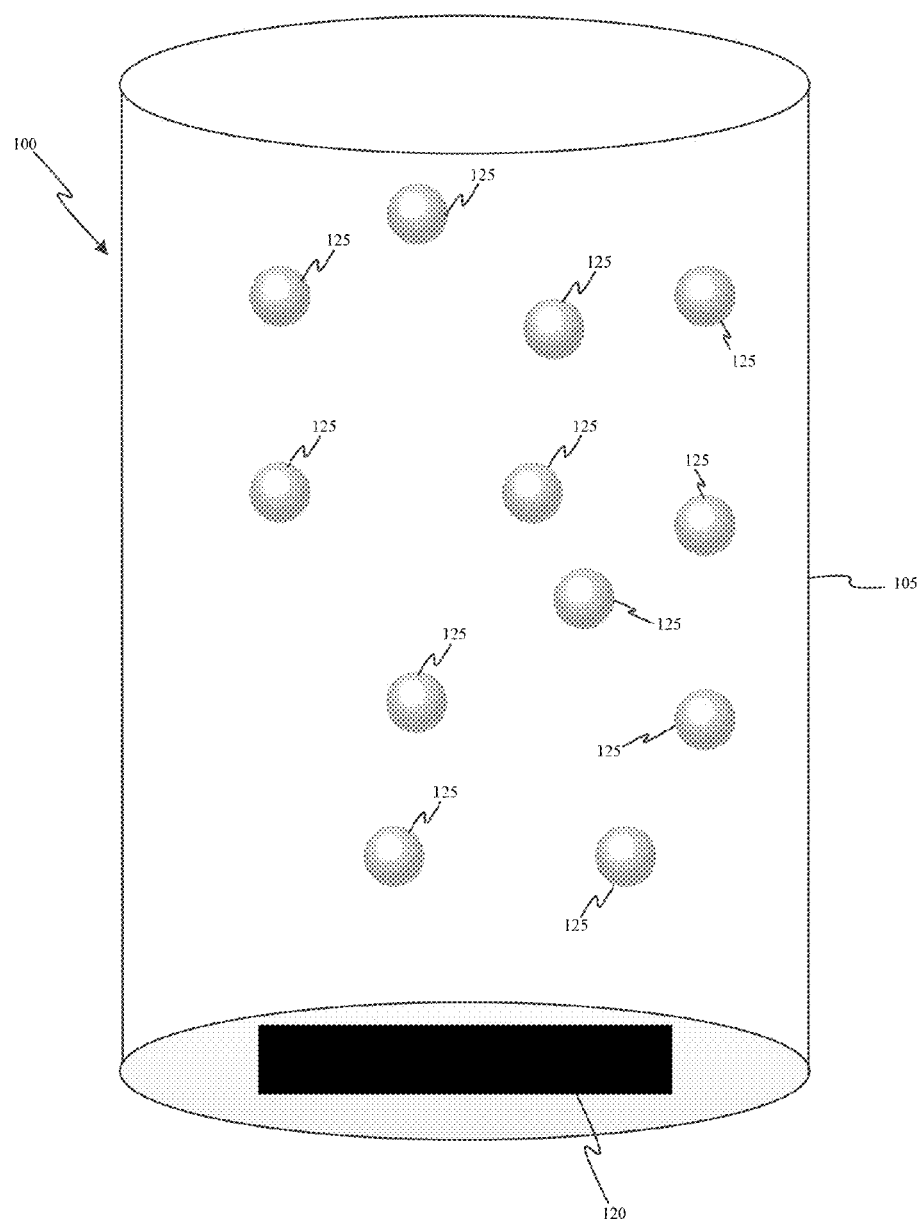
FIG. 1A depicts a block diagram of a container according to an embodiment.
Figure 1B:
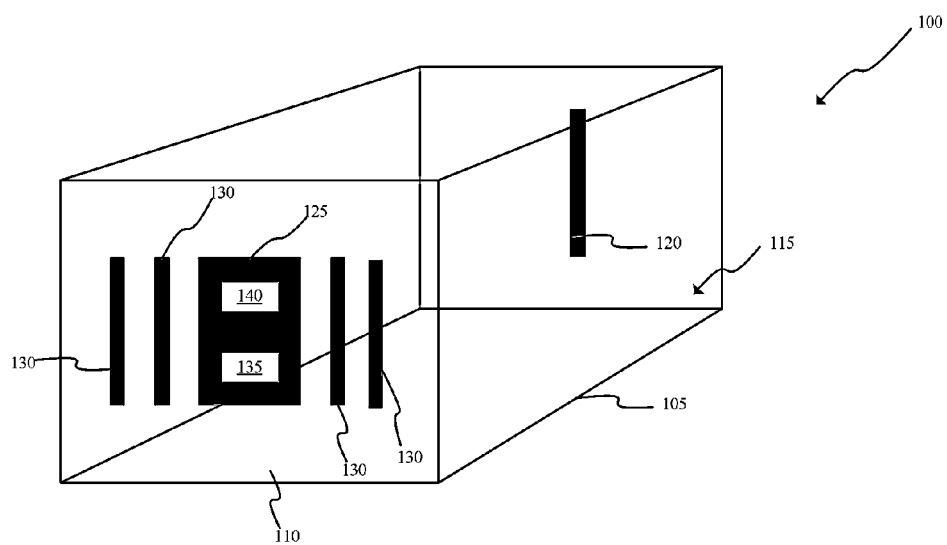
FIG. 1B depicts a block diagram of a container according to another embodiment.
Figure 1C:
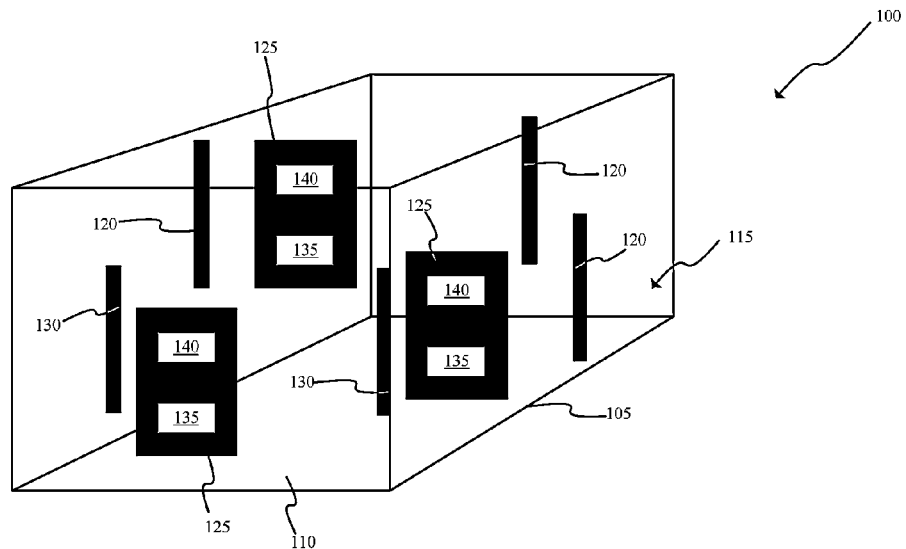
FIG. 1C depicts a block diagram of a container according to yet another embodiment.

FIGS. 1A through 1C each depict a block diagram of an illustrative container according to embodiments, generally designated 100. The packaging 100 may have a packaging material 105, one or more sensors 125 and one or more sound receiving devices 120. Examples of the container 100 may include, but are not limited to, a food container, a beverage container, a can, a drum, a tanker truck, a fuel storage tank, a fuel pipeline, a fuel tanker, a chemical storage tank, a chemical storage container, a swimming pool, an aquarium tank, an aerosol container, a water storage tank, a flexible liquid storage bladder, and a medical transport container.

The packaging material 105 may be any packaging material now known or later developed that is suitable for packaging and containing contents therein. Furthermore, the packaging material 105 may generally be suitable for protecting the contents contained therein from outside elements such as contamination, spoilage, and/or the like. Even further, the packaging material 105 may generally be used for the purposes of extending the usable life of the content contained therein. Examples of packaging materials may include, but are not limited to, metal-based packaging materials, polymer-based packaging materials, paper-based packaging materials, glass-based packaging materials and/or the like.

The packaging material 105 may be of any suitable shape or size for fully enclosing or partially enclosing the content contained therein. Furthermore, the packaging material 105 may be rigid in construction, or may be bendable, flexible or otherwise able to contort its shape to conform to the shape of the content contained therein. Accordingly, the packaging material 105 may also have any number of surfaces or faces.

The packaging material 105 may further be used to package any type of content, including, for example, solids, liquids, or gases. For the purposes of this disclosure, the content may generally be a liquid. Examples of liquids may include, but are not limited to oil, gasoline, kerosene, diesel fuel, water, salt water, fresh water, milk, juice, beer, alcohol, ethanol, methanol, organic solvents, wine, spirits, carbonated drinks, blood and medical fluids. The packaging material 105 may further be used for individual packaging or for bulk packaging. The packaging material 105 may also be marked with any type of indicia, including, but not limited to, labels, text, images, holograms, bar codes, matrix codes and/or the like.

In some embodiments, such as the embodiment shown in FIG. 1A, the container 100 may include a plurality of substantially free-floating sensors 125 and the sound receiving device 120 attached to the surface of the container 100. In other embodiments, such as the embodiment shown in FIG. 1B, the container 100 may include a single sensor 125, which may be affixed to a surface of the container 100, or may be free floating within the container, as described in greater detail herein. In other embodiments, such as the embodiment shown in FIG. 1C, the container 100 may include a plurality of sensors 125 that are each affixed to a surface of the container, and a plurality of sound receiving devices 120, as described in greater detail herein.

As is indicated in FIGS. 1A through 1C, the positioning and location of the one or more sensors and/or the one or more sound receiving devices 120 is not limited by this disclosure. In additional embodiments, the one or more sensors 125 and the one or more sound receiving devices 120 may each, individually, be implanted within a surface of the packaging material 105, such as, for example, an inside surface of the packaging material. In some embodiments, the sensor 125 and the sound receiving device 120 may each, individually, be affixed to a surface of the packaging material 105, such as, for example, an inside surface of the packaging material. In other embodiments, the sound receiving device 120 may be positioned on an outside surface of the packaging material 105. In other embodiments, the one or more sensors 125 may be able to move freely within the liquid inside the container 100. In other embodiments, the one or more sensors 125 may be tethered to an immobile object inside the container 100, such as an immobile object attached to the inside surface of packaging material 105. In other embodiments, the one or more sensors 125 may be tethered to a surface of the container 100, such as the inside surface of the packaging material 105. As shown in the embodiment of FIG. 1B, the plurality of sensors 125 may be affixed to a first surface 110, and the sound receiving device may be affixed to a second surface 115 of the packaging material 105, where the first surface is opposite the second surface. However, the positioning and relative locations of the one or more sensors 125 and the one or more sound receiving devices 120 are merely illustrative, and those skilled in the art will appreciate that other positions and configurations, such as the alternative positions and configurations discussed herein, may be possible without departing from the scope of the present disclosure.

The one or more sensors 125 may generally be any devices that are suitable for sensing one or more properties. The one or more sensors 125 may further be any devices that are suitable for emitting sound. Illustrative sensors may include, but are not limited to, a carbon dioxide sensor, an oxygen sensor, a biological oxygen demand sensor, a turbidity sensor, a pathogen sensor, a temperature sensor, an optic sensor, an analytic sensor, a chemical sensor, a pH sensor, a salinity sensor, a vibration sensor and an accelerometer. Illustrative properties that may be sensed by each sensor 125 may include, but are not limited to, color, turbidity, temperature, chemical composition, carbon dioxide content, oxygen content, presence of pathogens, pH, salinity, and vibration exposure.

The one or more sensors 125 may further be and/or incorporate any number of speakers, amplifiers, acoustic tags, sonar tags, graphene-based sensors and the like. The one or more sensors 125 may further be particularly suited for emitting sounds through liquid matter. A specific illustrative sensor 125 is an acoustic tag, such as the 0.5 g Model 800 Micro Acoustic Tag manufactured by Hydroacoustic Technology, Inc. of Seattle, Wash.

In some embodiments, such as, for example, the embodiments illustrated in FIGS. 1B and 1C, each sensor 125 may further be integrated with a digital signal processor 135 configured to direct the sensor to transmit a uniquely coded acoustic signal at a regular time interval in a frequency range. The uniquely coded acoustic signal may be a pulse having a combination of one or more different sound waveforms. Illustrative sound waveforms may include, but are not limited to, amplitude sinusoidal, frequency shifted, frequency modulated, pulse repetitions, and/or pulse trains. Alternatively, the uniquely coded acoustic signal may be a time-continuous spectrum of sound having amplitude peaks at frequencies for the classification of objects.

In some embodiments, such as, for example, the embodiments illustrated in FIGS. 1B and 1C, each sensor 125 may have a memory 140 in operable communication with the sensor. In some embodiments, each sound receiving device 120 may have a memory 140 in operable communication with the sound receiving device. The memory 140 may be configured to store any type of information, such as, for example, manufacturing information for the contents of the container 100, handling information for the contents of the container, detailed information about the contents of the container, and/or the like. The memory 140 may optionally be a standalone component. Alternatively, the memory 140 may be integrated within each sensor 125 and/or within each sound receiving device 120.

Each sensor 125 and/or each sound receiving device 120 may be in operable communication with one or more additional components 130 (as shown in FIGS. 1B and 1C), including, but not limited to, processing devices (CPUs), interface devices, display devices, communications ports, power sources such as batteries and the like, location transmitters such as global positioning satellite (GPS) transmitters and the like, radio frequency identification (RFID) transmitters, temperature sensors, carbon dioxide sensors, pathogen sensors, optic sensors, chemical sensors, microfluidic biochips, lab-on-a-chip devices and the like, as well as combinations thereof. The additional components 130 may each individually be integrated as a portion of each sensor 125, may each, individually, be integrated as a portion of each sound receiving device 120, may be individual standalone units or may be integrated into standalone units in combination with other additional components 130. In instances where one or more of the additional components 130 are not integrated as a portion of each sensor 125, the additional components may be implanted within a surface of the packaging material 105. Alternatively, the additional components 130 may be affixed to a surface of the packaging material 105. Each sensor 125 and/or each additional component 130 may be configured to provide real-time monitoring information, or may be configured to store monitoring information in the memory 140 for future access.

The additional components 130 may further be configured to monitor a plurality of properties of the content, such as, for example, turbidity, pH, toxin presence, pathogen presence, color, temperature, chemical composition, carbon dioxide ($CO_2$) content, location coordinates, and/or the like.

Each sound receiving device 120 may generally be any device that is suitable for receiving sound. Illustrative sound receiving devices may include, but are not limited to, omnidirectional microphones, unidirectional microphones, hydrophones and the like. Each sound receiving device 120 may further be particularly suited for receiving sounds through a liquid. One such specific example of a sound receiving device 120 may be a hydrophone having lead zirconate titanate (PZT) polycrystalline films on a titanium wire.

Figure 2:
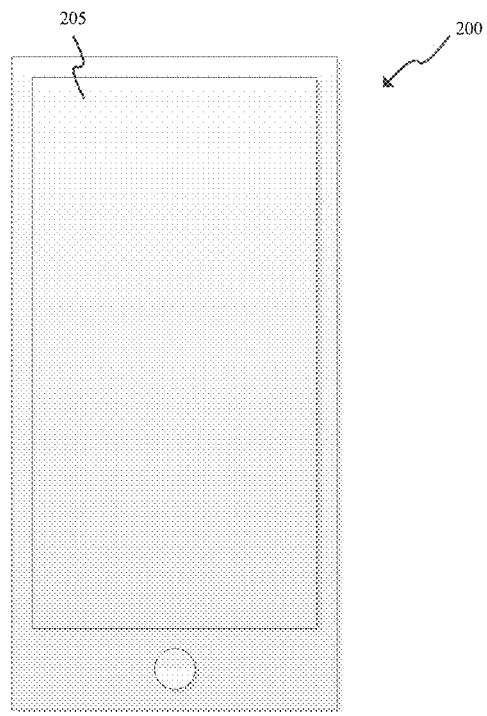
FIG. 2 depicts an electronic device for communicating with the container according to an embodiment.

Each sound receiving device 120 may further be configured to receive the uniquely coded acoustic signal from each sensor 125 and transmit the uniquely coded acoustic signal and/or additional information to an electronic device, such as the electronic device 200 depicted in FIG. 2. Communication of the acoustic signal and/or additional information from each sound receiving device 120 (FIGS. 1A-1C) may include, but is not limited to, wired communication, wireless communication and/or the like. Examples of wired communication may include, but are not limited to, universal serial bus (USB), FireWire, Thunderbolt, electrical power lines and the like. Examples of wireless communication may include, but are not limited to, radio waves, any IEEE 802.11 wireless networking standard, Bluetooth, near-field communication (NFC), radio frequency identification (RFID), infrared communication and the like. Each sound receiving device 120 may transmit any type of information to the electronic device 200 (FIG. 2), such as, for example, sensed information, status information, location information and/or the like.

Each sound receiving device 120 may further be configured as a sound, navigation and ranging (SONAR) device. Sound waves received by the SONAR device may generally have a frequency of about 50 Hz to a frequency of about 50 kHz and a combination of any discrete frequencies in between. Specific examples of frequencies received by a sound receiving device may include about 50 Hz, about 100 Hz, about 500 Hz, about 1 kHz, about 10 kHz, about 20 kHz, about 30 kHz, about 40 kHz and about 50 kHz, and may range between any two of these values, such as, for example, about 20 kHz to about 40 kHz. The SONAR device may further be configured to relate to passive SONAR principles known in the art.

Referring to FIG. 2, the electronic device 200 may be any device that includes a processor and tangible, computer-readable memory, and may further have a display 205. The display 205 may generally be a device for displaying images, text, video and the like, and may further be adapted to display the images, text, video and the like according to commands received from the processor. Examples of displays may include, but are not limited to, electroluminescent displays, electronic paper displays, vacuum fluorescent displays, light emitting diode (LED) displays, cathode ray tube (CRT) displays, liquid crystal displays (LCD), plasma display panels, digital light processing (DLP) displays, and organic light-emitting diode (OLED) displays. The electronic device 200 and/or the display 205 may further include a user interface such as a keypad, one or more switches or buttons, and/or a touch-sensitive screen. The touch-sensitive screen may receive contact-based inputs from a user, such as a user's fingers. The touch-sensitive screen may be adapted for gesture control, thus allowing for a user to tap, pinch, swipe or provide other similar gestures to elicit commands to the electronic device 200. The touch-sensitive screen may further be capable of sending touch commands to the processor. Illustrative touch-sensitive screens may include, but are not limited to, resistive touchscreens, capacitive touchscreens, infrared touchscreens and/or other technologies now known or later developed. The display 205 may be integrated as a component of the electronic device 200, or may be a standalone unit in operable communication with the electronic device 200.

The electronic device 200 may receive one or more communications from each sound receiving device 120 and/or each additional component 130 (FIGS. 1A-1C), and may use the processor to process and/or decode the one or more communications to obtain a result. The processor may process and/or decode information from the one or more communications by use of any signal processing techniques now known or later developed. Examples of signal processing techniques may include, but are not limited to filtering, adaptive filtering, denoising, spectrum analysis, digitization, reconstruction, storage, modulation, wavetable synthesis, pattern recognition, correlation analysis, prediction and the like.

The electronic device 200 may display the result on the display 205 in a format that may be readable to a user. The result may include any type of information gathered regarding the container 100 (FIGS. 1A-1C), any type of information gathered regarding the contents of the container or a combination thereof. The result may be real-time information, or may be information stored in the memory for future access. Examples of information that may be gathered may include, but is not limited to, conditions of the liquid such as color, temperature, chemical composition, pH, pathogen presence, toxin presence, carbon dioxide ($CO_2$) content and/or the like.

Figure 3:
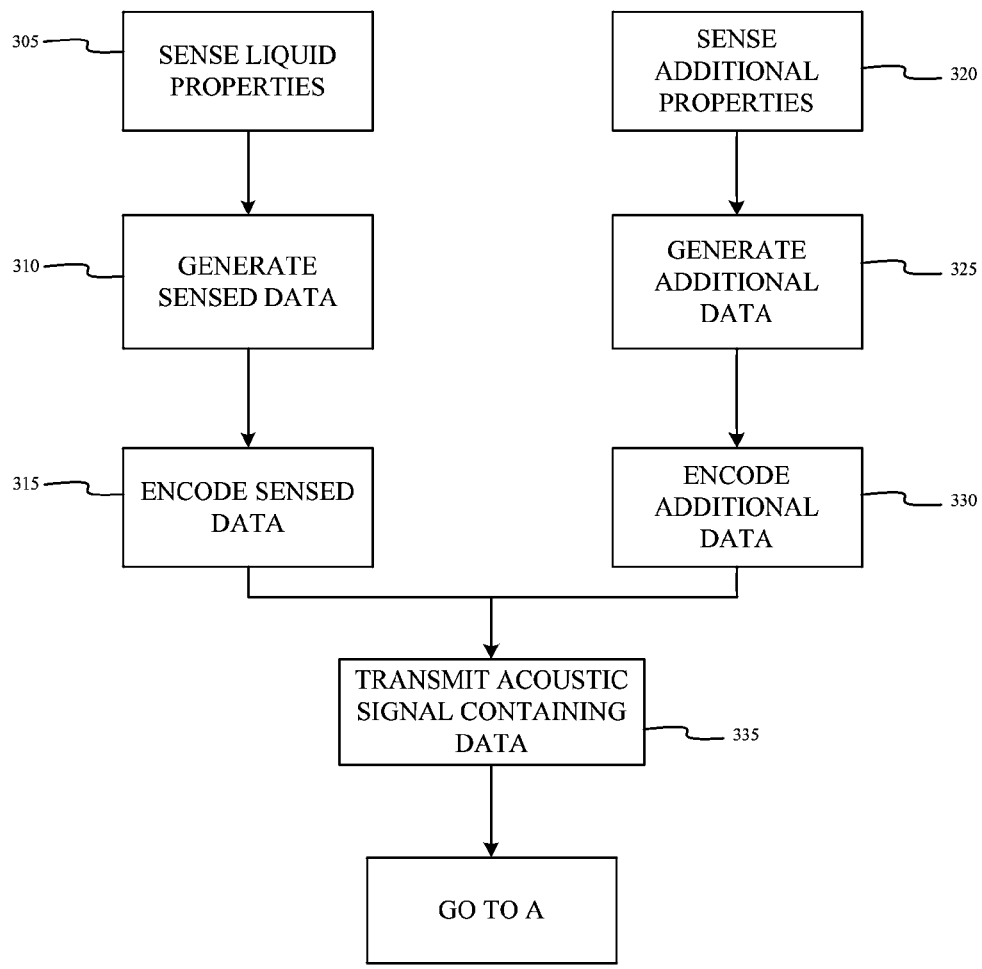
FIG. 3 is a flow diagram of a method of sensing a liquid and encoding sensed data within an acoustic signal for transmission according to an embodiment.

FIG. 3 is a flow diagram for a method for monitoring content within a container. The method may be carried out by a plurality of devices and/or components, as described herein. Each sensor may sense 305 one or more properties of the liquid contained within the container. Examples of properties that may be sensed may include, but are not limited to, color, temperature, chemical composition, pH, pathogen presence, toxin presence, carbon dioxide ($CO_2$) content and/or the like.

The system may generate 310 sensed data from the properties sensed. The sensed data may be any type of data and/or information that is culled from the properties of the liquid, and is not limited in scope by this disclosure. The system may generate 310 the data through the use of a processor, as described in greater detail herein.

The system may encode 315 the sensed data using any method of encoding now known or later developed. The data may generally be encoded 315 within an acoustic signal, as described in greater detail herein.

Each sensor and/or each additional component may sense 320 additional properties. In some embodiments, the additional properties may be related to the liquid contained within the container. In other embodiments, the additional data may not have any relation to the liquid contained within the container. In other embodiments, the additional data may be partially related to the liquid and partially unrelated to the liquid. Examples of additional properties may include, but are not limited to global positioning coordinates (GPS coordinates) of the location of the container, each sensor and/or each additional component, including present and past coordinates, echolocation of each sensor and/or each additional component, including past and present locations, a unique identifier of each sensor, liquid manufacturing information, liquid content information, handling information, date of manufacture of the liquid, location of manufacture of the liquid, instructions for disposing the liquid, instructions for recycling the liquid and/or the like.

The system may generate 325 additional data from the additional properties sensed. In some embodiments, the system may use a processor to generate 325 the additional data, as described in greater detail herein. The system may further encode 330 the additional data within an acoustic signal. In some embodiments, the additional data may be encoded 330 in an acoustic signal that is separate from the encoded sensed data. In other embodiments, at least a portion of the additional data may be encoded 330 in the same acoustic signal encoded with the sensed data. Each sensor and/or each additional component may transmit 335 the acoustic signal containing the sensed data and/or the additional data.

Figure 4:
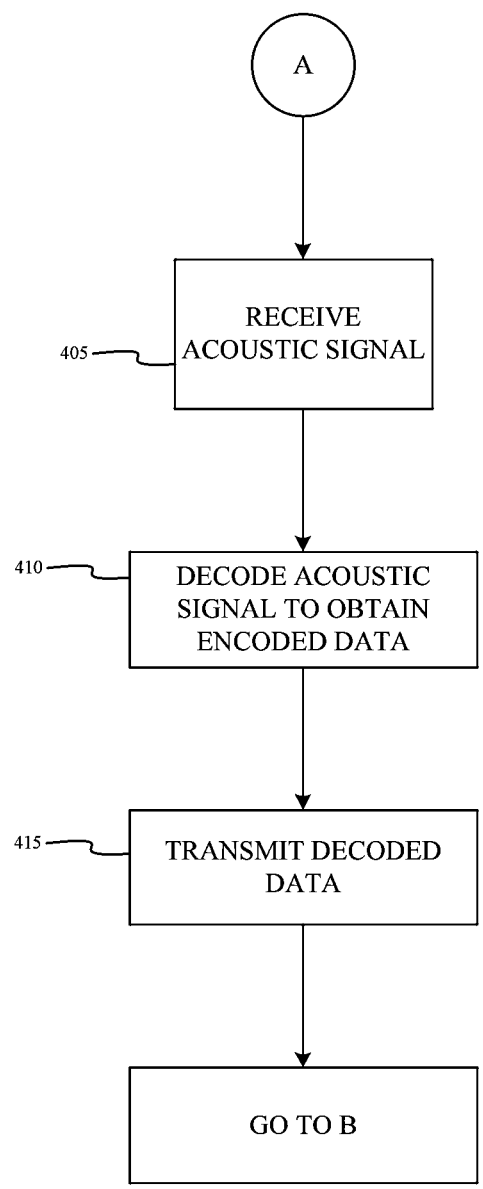
FIG. 4 is a flow diagram of a method of receiving and decoding an acoustic signal according to an embodiment.

FIG. 4 depicts a flow diagram of a method of receiving and decoding acoustic signals according to an embodiment. Each of the one or more sound receiving devices may receive 405 any number of acoustic signals that are transmitted by the sensors and/or the additional components. Each sound emitting device may be configured to receive 405 the signal from any direction. In addition, each sound emitting device may be configured to receive 405 the signal even in instances where the signal does not travel in a direct line from a sensor or an additional component, such as where the signal must travel around obstacles, corners and the like.

In certain embodiments, the acoustic signals may be altered or changed as they travel from each sensor and/or each additional component to each sound receiving device, which may be due to properties of the liquid through which the signal travels. Each sound receiving device may receive 405 the altered acoustic signal and, upon a determination that the signal has been altered, obtain additional information about the liquid. This may generally be achieved by assessing how the signal was altered and determining which properties of the liquid can cause the alteration. Each sound receiving device may generate data from the altered signal corresponding to the properties of the liquid.

Each of the sound receiving devices may decode 410 the acoustic signal to obtain the data encoded therein. The sound receiving devices may use a processor to decode 410 the acoustic signal. The decoded data may generally be the sensed data and/or the additional data, as described in greater detail herein.

Each of the sound receiving devices may transmit 415 the decoded data using any transmission protocol now known or later developed. Examples of transmission methods may include, for example, wired transmissions, wireless transmissions and/or the like.

Figure 5:
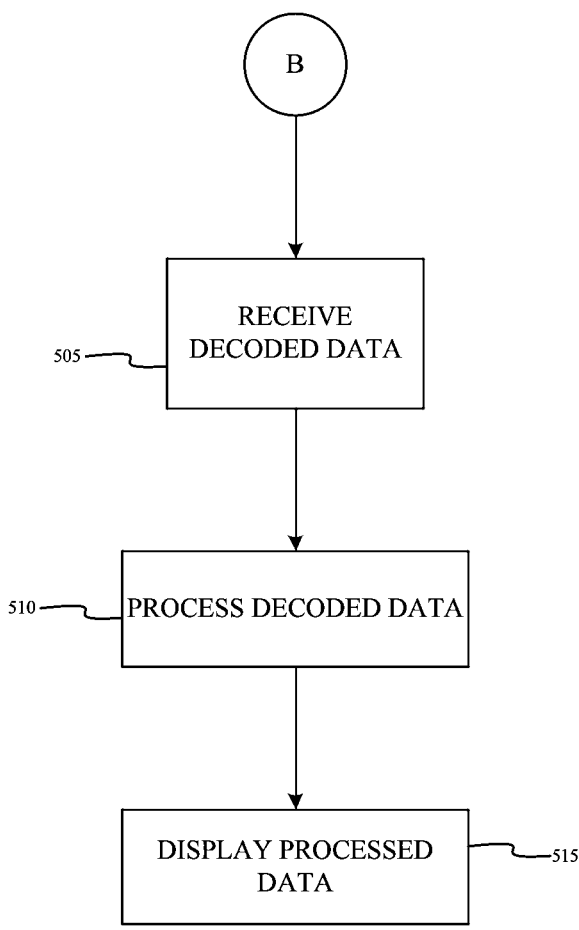
FIG. 5 is a flow diagram of a method of receiving, processing and displaying decoded sensed data according to an embodiment.

FIG. 5 depicts a flow diagram of a method for receiving data according to an embodiment. An electronic device may receive 505 the decoded data from one or more of the sound receiving devices. The decoded data may be received 505 via any transmission protocol now known or later developed, including, but not limited to, wireless transmissions, wired transmissions and/or the like.

The electronic device may process 510 the decoded data. Processing 510 the decoded data may include, for example, translating the decoded data into a user-readable format, compiling the decoded data, extracting portions of the decoded data and/or the like.

The electronic device may display 515 the processed data on the display. In some embodiments, the data may generally be displayed 515 in a format that is user-readable, user-searchable and/or the like. In some embodiments, the data may generally provide the user with information regarding the liquid, including the composition of the liquid, spoilage, manufacturing information, shipping history and/or the like, as well as other properties described in more detail herein.

In addition to the processed data, the electronic device may display 515 additional items, such as, for example, user input items that allow the user of the electronic device to complete additional tasks with the processed data. The additional tasks are not limited by this disclosure and may include, for example, transmitting the data to others, printing the data, manipulating the data, changing shipping information, ordering new liquid and/or the like.

FIG. 6 depicts a block diagram of illustrative internal hardware that may be used to contain or implement program instructions, such as a portion of the process steps discussed above in reference to FIGS. 3-5, according to embodiments. The internal hardware may be present in all of or a portion of the container, may be present in the electronic device, and/or may be present in both elements. A bus 600 serves as the main information highway interconnecting the other illustrated components of the hardware. A CPU 605 is the central processing unit of the system, performing calculations and logic operations required to execute a program. The CPU 605, alone or in conjunction with one or more of the other components disclosed in FIGS. 1 and 2, is an illustrative processing device, computing device or processor as such terms are used within this disclosure. Read only memory (ROM) 610 and random access memory (RAM) 615 constitute illustrative memory devices (i.e., processor-readable non-transitory storage media).

Program instructions, software or interactive modules for providing the interface and performing any querying or analysis associated with one or more data sets may be stored in the ROM 610 and/or the RAM 615. Optionally, the program instructions may be stored on a tangible computer readable medium such as a compact disk, a digital disk, flash memory, a memory card, a USB drive, an optical disc storage medium, such as a Blu-ray™ disc, and/or other non-transitory storage media.

An optional display interface 620 may permit information from the bus 600 to be displayed on the display 625 in audio, visual, graphic or alphanumeric format. Communication with external devices, such as, for example, communication between the container and the electronic device, may occur using various communication ports 630. An illustrative communication port 630 may be attached to a communications network, such as the Internet or an intranet, and may allow for direct communication between the container and the electronic device, as previously disclosed herein.

The hardware may also include an interface 635 which allows for receipt of data from input devices such as a keyboard 640 or other input device 645 such as a mouse, a joystick, a touch screen, a remote control, a pointing device, a video input device and/or an audio input device.

EXAMPLES

Example 1

Oil Monitoring System

An oil pipeline for transmission of oil from a source to any number of destinations may include a plurality of free-floating sensors within the oil and a plurality of sound receiving devices evenly spaced along the pipeline from the source to each destination. As the oil flows from the source to each destination, the sensors may travel along with the oil. Every time a sensor passes within the vicinity of a sound receiving device, it may transmit information regarding the oil to the sound receiving device, which in turn may transmit the information to a central computer, which can monitor the data for irregularities and the like and address problems as they arise.

Example 2

Food Container with Spoilage Sensor

Food containers, such as milk cartons and the like, may each be manufactured to contain a sensor and a sound receiver. The sensor may be configured to detect spoilage and transmit the monitoring information to the sound receiver, which in turn, can transmit sensed data in a wireless signal via 802.11b, Bluetooth, near field communication (NFC), and the like. Alternatively, the sound receiver may incorporate a display device with an updatable symbology, such as a barcode or a QR code for transmitting the sensed data. The sensor may be embedded or attached to the inside wall of the food container in order to prevent an end user from accidentally consuming the sensor. The shipper and the store selling the food may be equipped with devices, such as handheld scanners, that allow the user to scan each individual food container, determine the date it was packaged, its expected expiration date (if any), and whether the contents are safe for sale/consumption. Additionally, consumers may be able to view this information while shopping at the store by scanning the sound receiver with an electronic device, such as a smartphone, to determine whether they wish to purchase the item.

Example 3

Maintaining a Swimming Pool

A swimming pool monitoring apparatus may include one or more sensors and a sound receiver. The sensors may sense the conditions of the swimming pool and transmit an encoded signal to the sound receiver. The sound receiver may be connected to a system that monitors the pool conditions and can automatically dispense chemicals, water, cleaning materials and the like into the pool to regulate the pool with optimum conditions, thus eliminating the need for pool owners to manually monitor and maintain their pools. Additionally, the sound receiving device may be adapted to transmit a signal to an electronic device, such as the pool owner's smartphone or a maintenance person's smartphone to order additional supplies, to take additional actions and/or the like as necessary.

Example 4

Transportation of Medical Materials

A medical transport container may contain one or more sensors and a sound receiving device that are adapted to monitor the contents of the container, such as blood, organ transplant materials and/or the like. The sensors may sense the contents for changes in composition, temperature, and the like and transmit a signal to the sound receiving device. The sound receiving device may then provide the information to medical transport personnel, facilities, doctors and the like to ensure that the contents are safe for medical use.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system to monitor a liquid, the system comprising:
 a container comprising a packaging material configured to hold the liquid therein;
 one or more sensors disposed in the liquid and configured to sense one or more properties of the liquid and transmit an acoustic signal encoded with data regarding the sensed one or more properties through the liquid; and
 one or more sound receiver devices disposed in the liquid and configured to:
  receive the acoustic signal transmitted by at least one of the one or more sensors, and
  determine a location of the one or more sensors via echolocation.

2. The system of claim 1, wherein the one or more sound receiver devices include hydrophones and are further configured to decode the acoustic signal to obtain the data regarding the sensed one or more properties and transmit the data to an electronic device.

3. The system of claim 2, further comprising the electronic device that is configured to process the data obtained by and received from the sound receiver device to obtain content-related information.

4. The system of claim 1, wherein the container comprises one or more walls, wherein each of the one or more walls comprises an inside surface and an outside surface and wherein each of the one or more sensors:
 is affixed to the inside surface of at least one of the walls,
 is configured to move freely within the liquid and is not affixed to a surface of the container,
 is tethered to an immobile object within the container, or
 is tethered to the container.

5. The system of claim 4, wherein the container includes one of a food container, a beverage container, a can, a chemical storage container, an aerosol container, a flexible liquid storage bladder, and a medical transport container.

6. The system of claim 1, wherein the liquid includes one or more of oil, gasoline, kerosene, diesel fuel, water, salt water, fresh water, milk, juice, beer, alcohol, ethanol, methanol, organic solvents, wine, spirits, carbonated drinks, blood, or medical fluids.

7. The system of claim 1, wherein each of the one or more sensors comprises one or more of a carbon dioxide sensor, an oxygen sensor, a biological oxygen demand sensor, a turbidity sensor, a pathogen sensor, a temperature sensor, an optic sensor, an analytic sensor, a chemical sensor, a pH sensor, a salinity sensor, a vibration sensor, and an accelerometer.

8. The system of claim 1, wherein the one or more properties comprise one or more of color, turbidity, temperature, chemical composition, carbon dioxide content, oxygen content, presence of pathogens, pH, salinity, and vibration exposure.

9. The system of claim 1, wherein the acoustic signal is further encoded with a unique identifier corresponding to an identity of the sensor.

10. A method to monitor a liquid, the method comprising:
 sensing, using one or more sensors disposed in a packaging material that contains the liquid therein, one or more properties exhibited by the liquid;

producing, by the one or more sensors, data from the sensed one or more properties;

encoding, by the one or more sensors, the produced data into an acoustic signal;

transmitting, by the one or more sensors, the acoustic signal having the data encoded therein through the liquid to one or more sound receiver devices;

receiving the acoustic signal by one or more sound receiving devices; and detecting, by the one or more sound receiver devices, a location of each sensor via echolocation.

11. The method of claim 10, further comprising:

decoding the acoustic signal, transmitted by the one or more sensors and received by the one or more sound receiver devices, to obtain the data;

transmitting, by the one or more sound receiver devices, the data to an electronic device;

processing, by the electronic device, the data to obtain liquid-related information; and displaying, by the electronic device, the liquid-related information on a display.

12. The method of claim 10, wherein sensing the one or more properties comprises sensing one or more of color, turbidity, temperature, chemical composition, carbon dioxide content, oxygen content, presence of pathogens, pH, and salinity.

13. The method of claim 10, wherein transmitting the acoustic signal to the one or more sound receiver devices comprises transmitting a unique identifier corresponding to an identity of one of the one or more sensors.

14. An article of manufacture comprising:

a container comprising a packaging material configured to hold a liquid therein;

one or more sensors disposed within the packaging material and configured to sense one or more properties of the liquid and transmit an acoustic signal encoded with data regarding the sensed one or more properties through the liquid; and one or more sound receiver devices, each sound receiver device comprising a hydrophone and configured to:
receive the acoustic signal transmitted by the one or more sensors,
decode the acoustic signal to obtain the data, and
transmit the data to an electronic device.

15. The article of manufacture of claim 14, wherein each of the one or more sound receiver devices is configured to process the data encoded in the received acoustic signal to obtain content-related information.

16. The article of manufacture of claim 14, wherein the container has one or more walls comprising an inside surface and an outside surface and wherein each of the one or more sensors:
is affixed to an inside surface of at least one of the walls,
is configured to move freely within the liquid and is not affixed to a surface of the container,
is tethered to an immobile object within the container, or
is tethered to the container.

17. The article of manufacture of claim 14, wherein the container includes one of a food container, a beverage container, a can, a chemical storage container, an aerosol container, a flexible liquid storage bladder, and a medical transport container.

18. The article of manufacture of claim 14, wherein each of the one or more sensors comprises one or more of a carbon dioxide sensor, an oxygen sensor, a biological oxygen demand sensor, a turbidity sensor, a pathogen sensor, a temperature sensor, an optic sensor, an analytic sensor, a chemical sensor, a pH sensor, a salinity sensor, a vibration sensor, and an accelerometer.

19. The article of manufacture of claim 14, wherein the one or more properties comprise one or more of color, turbidity, temperature, chemical composition, carbon dioxide content, oxygen content, presence of pathogens, pH, and salinity.

20. The article of manufacture of claim 14, further comprising at least one memory in operable communication with the one or more sensors, wherein the memory is configured to store manufacturing information for the liquid, and handling information for the content and wherein the manufacturing information and the handling information are encoded in the acoustic signal.

21. The article of manufacture of claim 14, wherein each sensor is configured to encode the acoustic signal with a unique identifier corresponding to an identity of the sensor.

22. An article of manufacture comprising:

a container comprising a packaging material configured to hold a liquid therein;

one or more sensors disposed within the packaging material and configured to sense one or more properties of the liquid and transmit an acoustic signal encoded with data regarding the sensed one or more properties through the liquid; and one or more sound receiver devices configured to receive the acoustic signal transmitted by the one or more sensors and detect a location of each of the one or more sensors via echolocation.

* * * * *